United States Patent [19]

Tisdale

[11] Patent Number: 4,789,548
[45] Date of Patent: Dec. 6, 1988

[54] MEDICATION AND METHOD FOR TREATING HEARTWORMS IN DOGS

[76] Inventor: John W. Tisdale, 935 S. 3 Notch St., Andalusia, Ala. 36420

[21] Appl. No.: 855,471

[22] Filed: Apr. 24, 1986

[51] Int. Cl.$^4$ ............................................. A61J 3/06
[52] U.S. Cl. ................................... 424/472; 424/464; 424/474; 427/3
[58] Field of Search ............... 424/492, 489, 451, 463, 424/469, 474, 457, 468, 469, 465, 421, 472

[56] References Cited

U.S. PATENT DOCUMENTS

| | | | |
|---|---|---|---|
| 2,921,001 | 1/1960 | McDermott | 424/10 |
| 2,928,770 | 3/1960 | Bardami | 424/469 |
| 2,991,226 | 7/1961 | Millar et al. | 424/499 |
| 3,184,386 | 5/1965 | Stephenson | 424/471 |
| 3,279,997 | 10/1966 | Schenzer | 424/471 |
| 3,577,512 | 5/1971 | Shepherd et al. | 424/471 |
| 3,992,338 | 11/1975 | Estevenel et al. | 424/469 |

Primary Examiner—Thurman K. Page
Assistant Examiner—L. R. Horne
Attorney, Agent, or Firm—John M. Harrison

[57] ABSTRACT

A medication and method for treating heartworms in dogs, which medication includes a time release capsule or tablet dosage structure which is characterized either by discrete elements (capsule) or an outer layer or layers (tablet) of vasoconstricting and bronchial dilating medications and an inner, time-released layer or pellets of diethylcarbamazine. The vasoconstrictors and bronchial dilators are designed to counteract life-threatening vasodilation and bronchial constriction resulting from the release of acetylcholine by the dog when the heartworms are attacked by the diethylcarbamazine. The solid dosage structure can be constructed by layering such vasoconstrictors and bronchial dilators as prednisone, ephedrine, digoxin and dextroamphetamine sulfate in separate layers or combining these ingredients in a single layer separated from the diethylcarbamazine by a time-release substance such as gelatin. The capsule dosage structure includes discrete beads or elements of the medications in a capsule containing a time release, therapeutic dosage of the diethylcarbamazine. Alternatively, the vasoconstrictors and bronchial dilator medications can be injected or administered orally prior to treatment with the diethylcarbamazine according to the method of this invention.

13 Claims, 1 Drawing Sheet

MEDICATION AND METHOD FOR TREATING HEARTWORMS IN DOGS

BACKGROUND OF THE INVENTION

1. Field of the Invention

This invention relates to the treatment of heartworms or adult filaria in the heart and circulatory systems of dogs. More particularly, the invention relates to a combined preventative treatment and therapeutic treatment for dogs infested with adult filaria by using vasoconstrictors and bronchial dilators, as well as cardiac and sympathetic stimulants to counteract the effects of therapeutic treatment with diethylcarbamazine. Since it is speculated that the treatment of adult filaria with diethylcarbamazine results in the release of a toxin which causes the body to secrete acetylcholine, a chemical which acts to produce massive vasodilation and bronchial constriction in the animal, treatment of the adult filaria requires application of both preventative and therapeutic medicine. The preventative treatment is designed to use certain vasoconstricting, bronchial dilating and/or cardiac and sympathetic stimulant medication such as prednisone, ephedrine, digoxin and dextroamphetamine sulfate to counteract the undesirable vasodilation and bronchial constriction with resulting cardiac weakening in dogs which are treated with the diethylcarbamazine.

The adult heart worm parasite or "filaria" slowly and painfully kills hundreds of thousands of dogs annually. The parasite is particularly prolific in the coastal states, where it is estimated that at least 80 percent of all dogs which remain outside in mosquito-infested areas will have an infestation of heartworms before they reach three years of age. None of the currently used veterinary treatments are highly effective and safe, and most cause severe pain, swelling and in some cases, necroses of the tissues.

2. Description of the Prior Art

Diethylcarbamazine has been used for years under a variety of trademarks such as "Caricide", a trademark of the American Cyanimid Company, for the treatment of adult filaria or "filiariasis" in dogs. Caricide was used during Word War II to treat filiariasis in human patients in the south pacific theatre where infestation became a problem in American troops in that area. Diethylcarbamazine was used throughout the 1950's and 1960's by veterinarians as a successful treatment of healthy dogs for infestations of dirofilaria immitis, which is the most common species of adult filaria infecting dogs in the coastal United States. Sometime after the era of the 1960's, Caricide was discontinued due to complaints that various side effects and occasional deaths occurred from its use in heavily affected dogs having large numbers of worms in the heart. This supposed drug-sensitivity reaction was noted to be more prevalent in weak and emaciated dogs which were subjected to long-standing stress from the infestataions and it was observed to only occurr in a small percentage of those dogs treated.

U.S. Pat. Nos. 2,467,893, 2,467,894, and 2,467,895, dated Apr. 19, 1949, to Kushner, el al, U.S. Pat. No. 2,643,255, dated June 23, 1953, to Gustave, et al and U.S. Pat. No. Re. 23,701, dated Aug. 18, 1953, to Stewart, et al, disclose the use of carbamyl compounds as treating agents for filariasis in veterinary practice. U.S. Pat. No. 4,172,118, dated Oct. 23, 1979, to Baetz, discloses the use of diphenylamine as a detoxicant for drugs administered to animals.

I have found through extensive experience and observation in using the chemical Caricide or diethylcarbamazine, that upon absorption into the bloodstream of a dog and upon making contact with adult heartworms in the heart of the dog, the diethylcarbamazine causes release of a toxin by the heartworms into the bloodstream. This toxin causes the parasympathetic system of the dog to produce acetylcholine, which, in turn, causes massive vasodilation and bronchial constriction in the dog. This condition produces a sudden fall in blood pressure, resulting in respiratory depression, heart failure and death from shock, a syndrome which is similar to the effect caused by a bee sting or other toxic insect sting or bite. Some animals are hypersensitive to this toxin released by the heartworms and death occurs rapidly after treatment by the diethylcarbamazine. If the animal is not hypersensitive to the toxin and is not unduly affected by the massive vasodilation and bronchial constriction caused by the acetylcholine it will recover, since the adult heartworms are destroyed by contact with the diethylcarbamazine. I have noted that dogs which exhibit this hypersensitivity to the toxin released by the heartworms upon contact with the diethylcarbamazine have been saved by injections of adrenaline and atropine immediately after the reaction took place. Accordingly, the incorporation of anti-reactant medicines by injection, as well as in a capsule or tablet with the diethylcarbamazine on a time-release basis, will control the undesirable side effects resulting from massive vasodilation and bronchial constriction which causes weakening of the heart due to the toxin released by the adult heartworms and the acetylcholine produced by the body as a result of this toxin release. Specifically, it has been found that medications such as ephedrine, digoxin, dextroamphetamine sulfate and prednisone can be used as vasoconstrictors, bronchial dilators and cardiac and sympathetic stimulants, as well as anti-inflammatory agents, to counteract the effect of treating adult heartworms with diethylcarbamazine in a capsule or tablet dosage structure.

Accordingly, it is an object of this invention to provide a new and improved method and dosage structure for treating heartworms or filiariasis in dogs or other animals by initially pretreating the dogs by injection, tablets or capsules to effect vasoconstriction and bronchial dilation and subsequently introducing diethylcarbamazine into the blood stream for destroying the heart worms.

Another object of this invention is to provide a new and improved method for treating animals which are susceptible to filiariasis, by the steps of initially pretreating the animal with vasoconstrictors, bronchial dilators and cardiac and sympathetic stimulants and subsequently treating the adult heartworm condition with diethylcarbamazine.

Yet another object of the invention is to provide a method for treating dogs afflicted with filiarasis, which method includes the steps of administering ephedrine, digoxin, dextroamphetamine sulfate and prednisone to serve as vasoconstrictors, bronchial dilators, cardiac and sympathetic stimulants and anti-inflammatory agents, respectively, and subsequently treating the animal with diethylcarbamazine to kill the heartworms.

Yet another object of this invention is to provide a new and improved solid dosage structure for treating animals which are subject to filiariasis, which solid dosage structure is characterized by one or mroe pretreatment layers of a vasoconstrictor, bronchial dilator and cardiac and sympathetic stimulant and an inner, time-release treatment layer of diethylcarbamazine for killing the infestation of heartworms.

A still further object of the invention is to provide a new and improved solid dosage structure for treating filiariasis, which dosage structure is characterized by an outer coating of a palatable material such as sugar or the like, an inner coating of mixed ingredients which include a vasoconstrictor, bronchial dilator, cardiac and sympathetic stimulant and anti-inflammatory medication such as, for example, ephedrine, digoxin, dextroamphetamine sulfate and prednisone and an inner core of diethylcabamazine for killing the heartworms.

Another object of the invention is to provide a new and improved capsule or spansule dosage structure for treating filiariasis, which spansule is characterized by discrete pellets, beads or elements of a vasoconstrictor, bronchial dilator, cardiac and sympathetic stimulant and anti-inflammatory agent such as ephedrine, digoxin, and dextromphetamine sulfate and prednisone and a time release element or elements of diethylcarbamazine for killing the heartworms.

SUMMARY OF THE INVENTION

These and other objects of the invention are provided in a new and improved method and various dosage structures for treating filiariasis in animals uch as dogs, which method includes the steps of preventatively treating the animal by injection, tablets or capsules with selected vasoconstrictors, bronchial dilators and cardiac and sympathetic stimulants as well as an anti-inflammatory agent and subsequently therapeutically treating the animal with diethylcarbamazine. In a preferred embodiment of the invention, the vasoconstrictors, bronchial dilators, cardiac and sympathetic stimulants and anti-inflammatory agent include epherdrine, digoxin, dextroamphetamine sulfate and prednisone, which are incorporated in a tablet or capsule dosage structure as an outer layer, or shaped into discrete pellets, with a time-release inner layer, core or element(s) of diethylcarbamazine, to both pretreat and therapeutically treat the animal. Alternatively, the vasconstrictors, bronchial dilators, cardiac and sympathetic stimulants and anti-inflammatory agent can be injected and/or orally introduced into the animal and the diethylcarbamazine subsequently introduced after elapse of a predetermined time interval.

BRIEF DESCRIPTION OF THE DRAWING

The invention will be better understood by reference to the accompanying drawing wherein.

DESCRIPTION OF THE PREFERRED EMBODIMENTS

Figure 1:
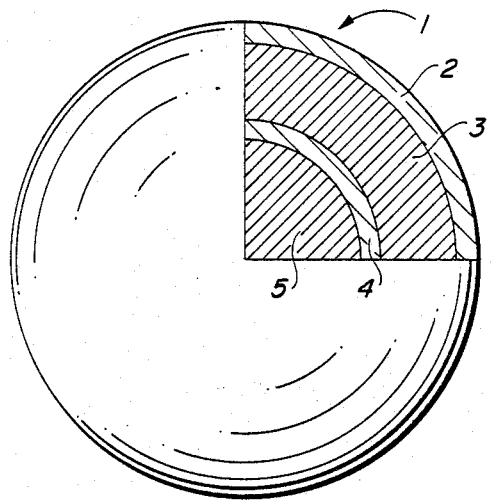
FIG. 1 is a spherically-shaped solid dosage structure having a sugar outer coating, a pretreatment layer inside the sugar coating and a diethylcarbamazine core.

Referring now to FIG. 1 of the drawing, in a preferred embodiment of the invention a mixed ingredient solid dosage structure is generally illustrated by reference numeral 1. The mixed ingredient solid dosage structure 1 includes a sugar coating 2 of selected thickness, a pretreatment layer 3 which consists of mixed vasoconstrictors, bronchial dilators and cardiac and sympathetic ingredients such as prednisone, ephedrine, digoxin and dextroamphetamine sulfate. A time-release layer 4 of selected thickness is provided adjacent and interiorally of the pretreatment layer 3 and shields a diethylcarbamazine core 5. Accordingly, it will be appreciated by those skilled in the art that when the mixed ingredient solid dosage structure 1 is administered to an animal such as a dog for the treatment of filiariasis, the animal readily ingests the mixed ingredients solid dosage structure 1 because of the sweet taste of the sugar coating 2. When the mixed ingredient solid dosage structure 1 is ingested, the sugar coating 2 rapidly dissolves and the pretreatment layer 3 is exposed, to release a mixture of selected vasoconstrictors, bronchial dilators and/or cardiac and sympathetic stimulants such as prednisone, ephedrine, digoxin and dextroamphetamine sulfate, into the dog's system. These drugs are designed to counteract massive vasodilation and bronchial constriction and the resulting cardiac weakening which results from the rapid lowering of blood pressure when the diethylcarbamazine core 5 is later dissolved and attacks the infestation of heartworms in the dog. Accordingly, the time-release layer 4 is designed to allow the respective pretreatment ingredients provided in the pretreatment layer 3 to have the desired biological effect on the dog prior to release of the diethylcarbamazine core element into the dog's system. When this desired preventative treatment has occurred and the diethylcarbamazine core is dissolved into the dog's system, release of acetylcholine from the body, which results from release of toxin from the heartworms upon contacting the diethylcarbamazine material, fails to produce the massive vasodilation and bronchial constriction which can be fatal to the dog and the dog has a much greater chance of recovery.

Figure 2:
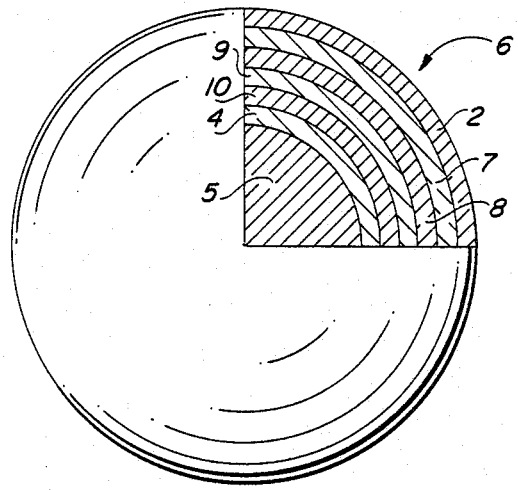
FIG. 2 is a spherically-shaped solid dosage structure characterized by a sugar outer coating, discreet layers of vasoconstrictors, bronchial dilators and cardiac and sympathetic stimulants and a diethylcarbamazine core.

Referring now to FIG. 2 of the drawing in another preferred embodiment of the invention a separate ingredient solid dosage structure 6 is illustrated, with a sugar coating 2, a prednisone layer 7, an ephedrine layer 8, a digoxin layer 9 and a dextroamphetamine sulfate layer 10, provided as discreet layers in the separate ingredient solid dosage structure 6. As in the case of the mixed ingredient solid dosage structure 1, a time-release layer 4 is provided between the diethylcarbamazine core 5 and the dextroamphetamine sulfate layer 10, in order to shield the animal's system from the effects of acetylcholine resulting from the toxin liberated from the heartworms upon contact with the diethylcarbamazine core, until the preventative ingredients have had an opportunity to cause vasoconstriction and bronchial dilation. It will be appreciated by those skilled in the art that the relative depth and/or position of the prednisone layer 7, ephedrine layer 8, digoxin layer 9 and the dextroamphetemine sulfate layer 10 in the separate ingredient solid dosage structure 6 is matter of choice, depending upon the relative order in which the respective ingredients are to be used to prepare the dog's system for attack by the acetylcholine responsive to liberation of the heartworm toxin.

Figure 3:
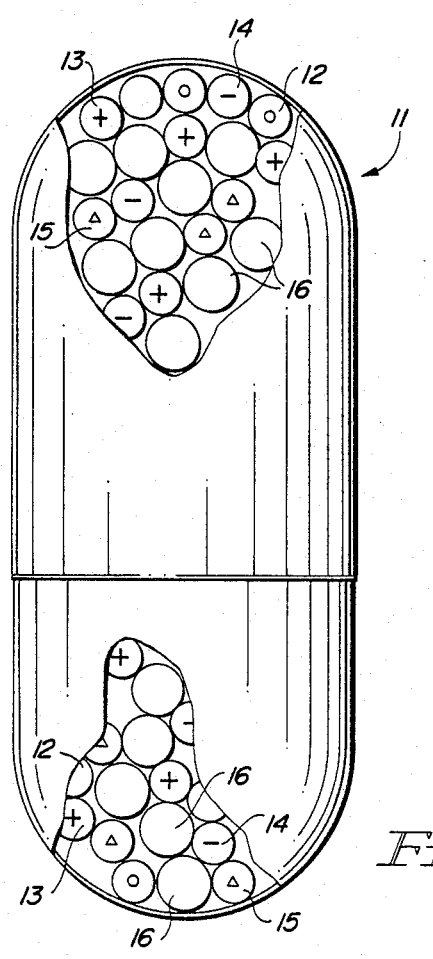
FIG. 3 is an elongated capsule containing discrete vasoconstricting, bronchial dilating and cardiac and sympathetic stimulating elements or pellets and time-release diethylcarbamazine structures or elements.

Referring now to FIG. 3 of the drawing in another preferred embodiment of the invention both the pretreatment and therapeutic ingredients for eliminating the heartworms are provided in a conventional gelatin capsule 11a, as a spansule dosage structure 11. Encapsulated inside the capsule 11a are discrete pretreatment prednisone pellets 12, ephedrine pellets 13, digoxin pellets 14 and dextroamphetemine sulfate pellets 15, as well as time-release pellets 16 of the therapeutic drug diethylcarbamazine. In a most preferred embodiment of this aspect of the invention, the diethylcarbamazine pellets 16 are coated with a layer of gelatin or other time-release material (not illustrated) to retard premature spreading of the diethylcarbamazine through a dog's system before the prednisone pellets 12, ephedrine pellets 13, digoxin pellets 14 and dextroamphetemine sulfate pellets 16 are absorbed in the blood.

It has been found that while the prednisone, ephedrine, digoxin and dextroamphetamine sulfate can be administered separately by injection or orally in tablet or capsule form prior to treatment with diethylcarbamazine, it is preferred to supply these ingredients in a solid dosage structure or a "spansule", as illustrated in FIGS. 1-3 and described above. However, whether the ingredients are administered separately in the mixed ingredient solid dosage structure 1, separate ingredient solid dosage structure 6 or spansule dosage structure 11, a preferred dosage is about 3 milligrams of prednisone, about ⅜ of a grain of ephedrine, about 0.25 milligrams of digoxin and about 2 to about 4 milligrams of dextroamphetamine sulfate, for a dog of average size, weighing about 40 pounds. It will, however, be appreciated by those skilled in the art that this dosage will vary, depending upon the size of the dog to be treated. In a most preferred embodiment of the invention the dosage is repeated twice daily at 8-hour intervals, for fourteen days. Furthermore, in each case where either the mixed ingredient solid dosage structure 1, the separate ingredient solid dosage structure 6 or the spansule dosage structure 11 is utilized, a 400 milligram dosage of diethylcarbamazine in each dosage structure, or 800 milligrams per day therapeutic treatment for a forty to sixty pound dog is indicated. The treatment is effective and inexpensive. The size and shape of the mixed ingredient solid dosage structure 1, separate ingredient solid dosage structure 6 and spansule dosage structure 11 can be varied, depending upon the relative dosages of the ingredients thereof which are necessary to treat dogs of various size according to the knowledge of those skilled in the art and the teachings of this invention. For example, both the mixed ingredient solid dosage structure 1 and the separate ingredient solid dosage structure 6 can be constructed in tablet form, as desired, according to the knowledge of those skilled in the art.

Generally, the time release layer 4 in the mixed ingredient solid dosage structure 1 and the separate ingredient solid dosage structure 6 and the time--release coating (not illustrated) on the diethylcarbamazine pellets 16 in the spansule dosage structure 11 can be designed to allow the anti-reactant medication to reach the bloodstream some 15-30 minutes before the diethylcarbamazine element is introduced into the system. This time delay insures that the reaction to the filaria toxin will not cause the massive vasodilation and bronchial contriction which would normally occur due to toxin release and acetylcholine secretion if the anti-reactant medication head not been used. While gelatin is a preferred material of choice for both the time-release layer 4 and construction of the capsule 11a, as well as the coating (not illustrated) provided on the time release pellets 16, other time-release coatings can be used in these applications, according to the knowledge of those skilled in the art.

It will be recognized that additional treatment may be necessary for some dogs, particularly under circumstances of severe emaciation caused by the filiarisis. Dogs in advanced stages of organic damage resulting from filaria infestations will not be aided by merely destroying the adult heartworms alone. Accordingly, the treatment is not recommended for dogs with severe liver disfunction syndrome, ascites, anemia, or other severely debilitated animals suffering from obvious organic damage. Such dogs are normally treated symtomatically before any heartworm treatment is used, including the treatment of this invention. Therefore, the primary advantage of the method or technique of treatment and the solid and spansule dosage structures of this invention lies in the fact that the inventive technique and various dosage structures safely kill all adult heartworms and all immature adult heartworms when used as noted herein. Accordingly, the method and dosage structure of this invention afford an economical and practical approach to controlling, as well as treating, adult and immature adult heartworms in reasonably healthy dogs not showing evidence of organic damge of a terminal nature.

The invention will be better understood by reference to the following examples:

EXAMPLE 1

A 50 pound, 6-year old female black and tan Coonhound was observed to have a bad cough and was noted to be in poor condition, short of breath and maciated, with micro-filaria present in the blood sample. The dog was treated by administering 400 milligrams of diethylcarbamazine twice daily on an 8-hour schedule after pretreating the dog with 0.25 milligrams of digoxin, ⅜ of a grain of ephedrine and 5 milligrams of prednisone thirty minutes prior to dosing on the diethylcarbamazine. A 14-day treatment was administered without observation of any adverse reaction due to toxin release by the treated heartworms. The dog made rapid progress back to normal health and showed dramatic improvement in breathing and stamina over a six week period of time after treatment. Blood samples checked negative for microfilaria at six weeks after adult treatment of the heartworms using this method.

EXAMPLE 2

A 50-pound, five-year old male Foxhound was observed to have a chronic cough, weight loss and tested positive on direct smear for microfilaria. Adult infestation of heartworms was diagnosed. 0.25 milligrams of digoxin, ⅜ of a grain of ephedrine and 5 milligrams of prednisone was administered thirty minutes prior to administering 400 milligrams of diethylcarbamazine orally at a rate of 400 milligrams twice daily. Treatment was carried out for fourteen days and six weeks later the dog was observed to be in good physical condition. Very small numbers of microfilaria were found in the blood during examination and the general condition of the dog was noted to be excellent.

EXAMPLE 3

A 28 pound, 8-year old spayed female mixed-breed dog was observed to have a bad cough and a wheezing sound on respiration. The dog was given a premedicated treatment of 0.15 milligrams of digoxin, ⅛ grain of ephedrine and 3 milligrams of prednisone by mouth in tablet form, before each dose of diethylcarbamazine of 300 miligrams, twice daily, on a 8-hour schedule was administered. No adverse reaction was observed. The cough was observed to be greatly improved in three weeks and six weeks later the cough was gone. However, it was recommended to continue giving the dog 0.15 milligrams of digoxin for several months on a daily basis, since some cardiac insufficiency was observed. The wheezing in the lungs was absent after six weeks and the dog appeared to be near normal.

EXAMPLE 4

A 60 pound, 6-year old male Pointer was observed to be very athlethic but had a violent cough after 30 minutes in the field. The dog would stagger and finally fall over and lie down. Pulmonary arterial blockage by heartworms was tentatively diagnosed and a blood smear tested positive for microfilaria in large numbers. A premedication treatment of 0.25 milligrams digoxin, ⅜ of a grain of ephedrine and 5 milligrams of prednisone was administered thirty minutes prior to dosing on 400 milligrams of diethylcarbamazine, twice daily on an 8-hour schedule for fourteen days. The dog's improvement was observed to be dramatic and six weeks later he was checked and found to be in excellent condition.

EXAMPLE 5

An 18-pound, 10-year old female mixed-breed dog was observed to have breathing problems, with a chronic cough. Multiple microfilara were found in blood tests and heartworm infestation was diagnosed. A premedication treatment of 0.15 milligrams of digoxin, 3 milligrams of prednisone and ⅛ of a grain of ephedrine for fourteen days was administered, along with following therapeutic treatment of 200 milligrams of diethylcarbamazine on an 8-hour schedule, twice daily. The dog had no apparent side effects and breathing and cough were much improved upon observation after treatment. The dog's appetite returned rapidly and recovery was observed to be complete.

The process and dosage structure of this invention facilitates an effective treatment of dogs for filariasis in a safe and effective manner by neutralizing the acetylcholine produced by the body resulting from diethylcarbamazine-induced toxin produced by the heartworms before the acetylcholine can adversely affect the dog. The treatment is effective using drugs which are well known as vasoconstrictors, bronchial dilators and cardiac and sympathetic stimulants, thus employing an anti-reactant feature prior to therapeutic treatment in order to render the old and well known diethylcarbamazine medicine safe and effective for its intended use.

It will be appreciated by those skilled in the art that while vasoconstricting, bronchial dilating and cardiac and sympathetic stimulants as well as anti-inflammatory agents may all be used to brace a dog's system for attack by acetylcholine secretions, any combination of these drugs can be used as deemed necessary by those skilled in the art, for treatment of a specific dog in question. Furthermore, known vasoconstrictors, bronchial dilators, cardiac and sympathetic stimulants and anti-inflammatory agents other than prednisone, ephedrine, digoxin, and dextroamphetamine sulfate can be used to pretreat the animals in preparation for therapeutic dosages of the diethylcarbamazine, also according to the knowledge of those skilled in the art. For example, while prednisone is a known vasoconstricting and bronchial dilating steroid which also has good anti-inflammatory properties, other steroids such as cortesone can also be used in the method and medication of this invention. Furthermore, the digoxin serves not only as a mild vasoconstrictor and bronchial dilator, but also operates primarily as a heart muscle stimulant to elevate the blood pressure in dogs treated according to the method and medication of this invention. Other known medications can also be used to achieve this goal of cardiac muscle stimulation according to the knowledge of those skilled in the art. Ephedrine has been found without equal in my experiments as a vasoconstricting and bronchial dilating medication. Accordingly, by experimentation, I have found that complete and effective pretreatment of a dog for filiariasis can be effected using the drugs prednisone, ephedrine and digoxin. The addition of dextroamphetamine sulfate, another known vasoconstricting and bronchial dilating drug, also serves to help stimulate the central nervous system in a dog in order to counteract the depressant effect of the acetylcholine, as well as to aid the vasoconstricting and bronchial dilating functions. Under circumstances where the pretreatment medication can be administered by injection, it has been found that adrenalin and prednisone, as well as atrophine can be used to good advantage. Dextroamphetamine sulfate can also be injected in a liquid medium to pretreat a dog prior to administration of the diethycarbamazine.

While the preferred embodiments of the invention have been described above, it will be recognized and understood that various modifications may be made therein and the appended claims are intended to cover all such modifications which may fall within th spirit and scope of the invention.

Having described my invention with the particularity set forth above, what is claimed is:

1. A solid dosage structure for treating filiariasis in animals comprising a diethylcarbamazine core, a first layer of time-release material encapsulating said core and a second layer comprising at least one vasocontricting medication and at least one bronchial dilating medication covering said first layer of time-release material, said vasoconstricting and bronchial dilating medications are ephedrine and dextroamphetamine sulfate respectively.

2. The solid dosage structure of claim 1 wherein said time-release material is gelatin.

3. The solid dosage structure of claim 1 wherein said vasoconstricting and bronchial dilating medication is selected from the group consisting of ephedrine and dextroamphetamine sulfate.

4. The solid dosage structure of claim 1 wherein said first layer further comprises a cardiac stimulant medication and a central nervous sytem stimulant medication.

5. The solid dosage structure of claim 4 wherein said time-release material is gelatin.

6. The solid dosage structure of claim 1 further comprising a third layer containing at least one cardiac stimulant, at least one central nervous system stimulant and at least one anti-inflammatory medication, said third layer covering said second layer in said dosage structure.

7. The solid dosage structure of claim 6 wherein said vasoconstricting and bronchial dilating medication is ephedrine, said cardiac stimulant is digoxin, said central nervous system stimulant is dextroamphetamine sulfate and said antiinflammatory medication is prednisone.

8. The solid dosage structure of claim 3 further comprising a third layer of digoxin covering said second layer and a fourth layer of prednisone covering said third layer.

9. The solid dosage structure of claim 1 wherein said vasoconstricting and bronchial dilating medication is ephedrine and further comprising a third layer of digoxin covering said second layer, a fourth layer of prednisone covering said third layer and a fifth layer of dextroamphetamine sulfate covering said fourth layer.

10. The solid dosage structure of claim 9 further comprising a sugar coating substantially encapsulating said fifth layer of dextroamphetamine sulfate.

11. A solid dosage structure for treating filiarisis in dogs comprising a diethylcarbamazine core, a first layer of a non-medicating material encapsulating said core, a second layer of a vasoconstricting and bronchial dilating medication covering said first layer; a third layer of a cardiac stimulant covering said second layer; a fourth layer of a central nervous system stimulant covering said third layer; and a fifth layer of an anti-inflammatory medication covering said fourth layer.

12. The solid dosage structure of claim 11 wherein said second layer is ephedrine, said third layer is digoxin, said fourth layer is dextroamphetamine sulfate and said fifth layer is prednisone.

13. The solid dosage structure of claim 12 further comprising a sugar coating substantially encapsulating said fifth layer of prednisone.

* * * * *